United States Patent
Campbell et al.

(10) Patent No.: US 8,927,006 B2
(45) Date of Patent: Jan. 6, 2015

(54) METHODS AND COMPOSITIONS FOR RAPID TREATMENT OF OTITIS EXTERNA

(75) Inventors: William R. Campbell, Jamestown, NC (US); Neil E. Paulsen, High Point, NC (US); Roland H. Johnson, Lexington, NC (US); Douglas I. Hepler, McLeansville, NC (US)

(73) Assignee: Bayer Healthcare LLC

( * ) Notice: Subject to any disclaimer, the term of this patent is extended or adjusted under 35 U.S.C. 154(b) by 144 days.

(21) Appl. No.: 12/943,810

(22) Filed: Nov. 10, 2010

(65) Prior Publication Data
US 2011/0281809 A1 Nov. 17, 2011

Related U.S. Application Data

(60) Provisional application No. 61/260,309, filed on Nov. 11, 2009.

(51) Int. Cl.
| | | |
|---|---|---|
| *A61K 47/14* | (2006.01) | |
| *A61K 9/107* | (2006.01) | |
| *A61K 9/127* | (2006.01) | |
| *A61K 45/06* | (2006.01) | |
| *A61K 9/00* | (2006.01) | |
| *A61K 31/496* | (2006.01) | |
| *A61K 31/573* | (2006.01) | |
| *A61K 36/752* | (2006.01) | |

(52) U.S. Cl.
CPC ................. *A61K 45/06* (2013.01); *A61K 47/14* (2013.01); *A61K 9/107* (2013.01); *A61K 9/0046* (2013.01); *A61K 9/127* (2013.01); *A61K 31/496* (2013.01); *A61K 31/573* (2013.10); *A61K 36/752* (2013.01)
USPC .......................................... 424/450; 514/786

(58) Field of Classification Search
None
See application file for complete search history.

(56) References Cited

U.S. PATENT DOCUMENTS

| 5,891,913 A * | 4/1999 | Sallmann et al. ............. 514/567 |
| 2005/0013854 A1* | 1/2005 | Mannino et al. .............. 424/450 |
| 2005/0159369 A1* | 7/2005 | Lane .............................. 514/28 |
| 2007/0078116 A1 | 4/2007 | Lane |
| 2008/0124385 A1 | 5/2008 | Campbell |
| 2008/0206161 A1 | 8/2008 | Tamarkin et al. |
| 2009/0005339 A1 | 1/2009 | Scholz et al. |
| 2009/0082337 A1 | 3/2009 | Venkastesh et al. |
| 2009/0111780 A1* | 4/2009 | Giordano ...................... 514/171 |

FOREIGN PATENT DOCUMENTS

| WO | WO 95/20944 A1 | 8/1995 | |
| WO | WO 99/20259 A2 | 4/1999 | |
| WO | WO01/85159 | * 11/2001 | ............. A61K 31/19 |
| WO | WO 2005/009436 A1 | 2/2005 | |
| WO | WO 2005/077360 A2 | 8/2005 | |
| WO | WO 2006/029074 A2 | 3/2006 | |
| WO | WO 2006/099325 A2 | 9/2006 | |
| WO | WO 2008/036292 A2 | 3/2008 | |

OTHER PUBLICATIONS

Chemical Abstracts Registry entry 4080-31-3, (1-(3-chloro-2-propenyl)-3,5,7-triaza-1-azoniadamantane chloride) entered into STN Nov. 16, 1984.*
Merriam-Webster's Collegiate Dictionary, Tenth Edition, published 1998 by Merriam-Webster, Incorporated, p. 924.*
Communication from European Patent Office from application No. EP 201080051245.7, (2013).

* cited by examiner

*Primary Examiner* — Eric Olson

(57) ABSTRACT

Methods for treating and preventing otitis externa with a course of treatment consisting of as little as a single dose are provided. The methods are practiced by topical administration of compositions having a lipid carrier, such as liposomes and non-vesicular lipids, to the outer ear canal. Such compositions lack viscocity-enhancing celluloses or adhesives, and are preferably not in the form of a gel. Active agents useful for treating pain, inflammation, fungal or parasitic infestation and/or infections in the outer ear are co-administered in or with the composition.

16 Claims, No Drawings

METHODS AND COMPOSITIONS FOR RAPID TREATMENT OF OTITIS EXTERNA

CROSS REFERENCE TO RELATED APPLICATION

This application is based on and claims benefit of priority benefit under 35 U.S.C. §119(e) to U.S. Provisional Application No. 61/260,309 filed on Nov. 11, 2009, the disclosure of which is hereby incorporated by reference in its entirety for all purposes.

FIELD OF THE INVENTION

The present invention relates to non-invasive methods and compositions for treating otitis externa (outer ear infection or infestation and inflammation) without use of a cellulose viscocity-enhancing component, gel or adhesive-based formulation.

BACKGROUND OF THE INVENTION

Millions of animals and people, especially children, are affected each year with otitis externa; i.e., infection and/or infestation of the outer ear, often accompanied by painful inflammation of the affected tissue. Animals with ear flaps, such as many breeds of dogs, are especially susceptible. Their covered outer ear canals provide an inviting environment for microbes to breed and inflammation to form, yet caretakers may not notice the condition as readily as in raised ear animals.

A variety of bacteria, viruses and fungi can be responsible for causing otits externa. Often first-line treatment is limited to oral or topical antibiotics. The use of orally administered medications may be diluted by the systemic distribution of the drug, and could place the patient at risk for side effects associated with systemic delivery (e.g., yeast infections in females). Yet the risk for fungal overgrowth in the ear canals of patients treated only with topical antibiotics for bacterial infections emphasizes a need for careful diagnosis and treatment of all the causative agents associated with otitis externa and its sequalae (Schraeder and Issacson, *Pediatrics,* 111(5): 1123, 2003). As such, a preference is emerging for multiple agent topical treatment of otitis externa, especially in children and animals in whom compliance with a long-term oral dosing regimen can be difficult to obtain.

When single or multiple active agents are applied topically to treat otitis externa, efficacy often depends on how long the medication can be maintained in contact with the affected tissue, especially when a fungal or parasitic infestation (e.g., ear mites) is present. Conventional ear drops are problematic because the tissues they contact is directly affected by the attitude of the patient's head, and the drops can easily flow out of the ear with movement. Approaches to increasing the residence time of topical medications in the external ear canal have included use of flowable gels made more adhesive with a cellulose (e.g., hydroxypropyl methylcellulose), gel plugs, mousses, foams, or other formulations with adhesive properties.

Yet compliance with dosing regimes using such formulations is again an issue, as their thick and/or sticky feel in the ear may be a source of frustration, especially to animals and young children. If acceptance of a retainable topical formulation isn't possible, the remaining option is often more frequent, and less convenient, dosing with less viscous solutions, such as conventional ear drops. A need, therefore, exists for an approach to topical treatment of otitis externa which doesn't rely on use of gels, cellulose-based or adhesive compositions, and which can be applied infrequently (i.e., once or twice as an entire course of treatment) to ameliorate (significantly reduce symptoms) or resolve the condition.

SUMMARY OF THE INVENTION

The invention provides a multiple agent composition for treating antibiotic or parasitic infections, fungal infestations, and inflammation which can be placed into and retained in the ear for a sufficient length of time to treat otitis externa without use of a gel, cellulose or other adhesive formulation. Surprisingly, it has been found that formulations of the invention can be applied as infrequently as once, with an optional supplemental dosing, to resolve the treated condition entirely.

Preferred medicaments for delivery according to the invention are those useful in the treatment or prevention of otitis externa and its sequelae (such as pruritis). The invention is particularly well-suited to the delivery of medicaments such as antibiotics or anti-viral agents (depending on the source of the infection present), anti-fungal agents, and anti-inflammatory agents or other painkillers. For prevention of chronically recurring external ear infections, the methods of the invention may also be utilized between active infections to deliver prophylactic agents to the outer ear canal.

The summary of the invention described above is not limiting and other features and advantages of the invention will be apparent from the following detailed description of the preferred embodiments, as well as from the claims.

DETAILED DESCRIPTION OF THE INVENTION

A. Methods for Topical Treatment of Otitis Externa

The present invention provides methods for topically treating and preventing otitis externa through administration of multiple active agents, preferably at least two and most preferably at least three active agents, which are useful in prophylaxis or treatment of external ear infections, infestations and inflammation. By "topical administration" is meant that a composition of the invention is applied to the external ear canal; i.e., on the outer ear side of the tympanic membrane (eardrum). The compositions of the invention do not contain gelling agents, methylcellulose or other adhesive elements, yet are sufficiently potent to ameliorate or resolve otitis externa through a single dose course of treatment.

Topical administration to the outer ear canal is achieved via, for example, introducing the composition of the invention into the outer ear canal via any medically acceptable means; e.g., by applying the carrier composition to the membrane by insertion of a needleless syringe, dropper or swab into the auditory canal. Administration is repeated as required to achieve the therapeutically effective dosage level for the antibiotic compound given. However, a particular advantage offered by the invention is that it enables amelioration (substantial reduction of symptoms) or resolution (elimination of symptoms) of otitis externa with a course of treatment consisting of as little as one dose.

If the otitis externa proves to be unusually refractive to treatment, but the clinical symptoms of the condition are ameliorated after the first dose administered, a follow up dose can be delivered after a medically suitable period of time. For example, as demonstrated in Example 1, 10 to 20 drops of a topical carrier composition could be delivered once, with a follow up dose at day 14 following treatment, or day 7 in the event of severe symptoms, if clinical observations of the patient's condition indicate that the first dose administered didn't completely resolve the condition. Those of ordinary skill in the art will be familiar with, and readily able to select, dosing regimens suitable for following to treat a particular infection.

B. Lipid-Based Carriers for Use in the Invention

Presently preferred topical carriers for the actives applied according to the invention are those that are lipid-based, such as lipid emulsions (including microemulsions and oil-in-water emulsions), as well as lipid vesicles, such as liposomes, liosomes, micelles and transfersomes (ultraflexible lipid vesicles). Phospholipid-based formulations are presently preferred, especially for the non-vesicular formulations useful in the invention.

Most preferably, the medicament delivered according to the invention is preferably carried in a lipid phase (e.g., in the lipid bilayer of a liposome) rather than in an aqueous phase (e.g., in the core of a liposome). Thus, lipid-soluble medicaments (which can generally be provided at a higher concentration in the lipid layer of a vesicle than a water-soluble medicament dispersed in an aqueous phase can be) are preferred, though not required, for use in the invention.

Methods for preparing lipid emulsions and vesicles are well-known in the art, and so will only be briefly outlined here with respect to the most presently preferred embodiment of topical carrier composition for use in the invention, a liposome prepared without a steric stabilizer, and without a viscocity-enhancing, gelling and/or adhesive agent.

By "liposome" is meant a spherical lipid vesicle bounded by an ordered lipid bilayer and enclosing an aqueous phase. The lipid bilayer of liposomes is usually made of natural or synthetic phospholipids, but can also be made of non-phospholipids. The lipid bilayer of liposomes is an ordered bilayer, meaning that the molecular "head" and "tail" structures of the lipids are lined up next to one another.

Liposomes utilized in the present invention can be unilamellar (having one lipid bilayer) or more preferably are multilamellar. Liposomes that are "multilamellar" have multiple layers or membranes. This type of liposome has layers of lipid bilayers with an aqueous fluid spaced in between the lipid bilayers. Multilamellar liposomes have at least two layers of lipids.

Preferred liposomes are those described herein, and in commonly owned U.S. patent application Ser. No. 10/366,584, filed on Feb. 12, 2003, the disclosure of which is incorporated herein in its entirety, by this reference. However, those of ordinary skill in the art will recognize that other formulations of liposomes may be utilized, including phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine. Such lipids will also be useful in non-vesicular topical carrier compositions of the invention.

The size of liposomes and lipid vesicles utilized in the present invention, if any, may be variable, but such vesicles are preferably of uniform size in each batch preparation. The liposomes may be up to 20 μm, 25 μm, or even 30 μm. But in preferred embodiments about 95% of the liposomes will be from about 0.5 μm to about 10 μm in diameter. In one embodiment, at least 80% of liposomes in a preferred composition manufactured according to the methods described herein are from about 0.5 μm to about 5 μm. In this respect, the term "about" encompasses a range of 5% upwards or downwards from the stated value. The actual diameters of the liposomes will be a function of the cooling curve followed and the length and vigor of stirring or vortex hydration, when those processes are used in the manufacture of the liposomes. In still other embodiments, the liposomes can be multilamellar liposomes where a single larger liposome encapsulates one or more smaller liposomes.

Conventional liposomes manufactured according to means well known in the art may be used in the invention, but the preferred liposomes of the present invention do not contain a lipid soluble preservative as found in liposomes of the prior art (see, e.g., U.S. Pat. Nos. 4,761,288 and 4,897,269, both to Mezei, are both hereby incorporated by reference in their entirety). Indeed, the compositions of the invention will preferably be preservative-free although, if necessary to the storage conditions, a water-soluble preservative may be utilized, such as a benezoic acid or a benzethonium salt (e.g., benzethonium chloride) or, most preferably, an oil-insoluble product such as DOWCIL™ 200 (oil-insoluble 96% cis 1-(3-chloroallyl)-3,5,7-triaza-1-azoniaadamantane chloride, Dow Biocides) or similar products known in the art, including other DOWCIL™ branded products.

However prepared, compositions of the invention do not include any methylcellulose or any other viscosity enhancing or gelling agents. By "viscosity enhancing or gelling agents" is meant an agent that is added to the composition to increase the viscosity. A viscosity enhancing agent will increase the viscosity of a composition by at least 10,000 centipoise at 25° C. Viscosity enhancing agents include, but are not limited to, methyl cellulose, hydroxypropyl methyl cellulose (HPMC), alginic acid, gelatin, acacia (gum Arabic) carbomer, and cetostearyl alcohol. Phospholipids are not considered viscosity enhancing agents within this definition.

If the liposome is a phospholipid based vesicle, a preferred lipid will be phospholipon 90H, which is obtained and purified from soy lecithin and has the chemical name 1,2-dia-cyl-5N-glycero-3-phosphatidyl choline. It is minimum 90% phophatidyl choline and is fully hydrogenated. But the person of ordinary skill will realize that other lipids may also be used in the present invention. For example, the phosphatidylcholine can be of lower purity, or can contain other lipids or carrier materials such as, for example, propylene glycol/ethanol, medium chain triglycerides, oil/ethanol, phosphatidic acid, cholesterol, and phosphatidylinositol. The phospholipid may be any natural or synthetic phospholipid, for example phosphatidylethanolamine, phosphatidylserine, phosphatidylinositol, phosphatidylglycerol, phosphatidic acid, lysophospholipids, egg or soybean phospholipid or a combination thereof. The phospholipid may be salted or desalted, hydrogenated or partially hydrogenated, natural, synthetic, or semi-synthetic. Examples of commercially available phospholipids include but are not limited to egg phospholipids P123 (Pfanstiehl, Waukegen, Ill.), Lipoid E80 (Lipoid, Ludwigshafen, Germany); and the hydrogenated soy phospholipids Phospholipon 80H®, 80G®, 90H® and 100H® (Nattermann, Munich, Germany) and 99% pure soy phosphatidyl choline (Avanti Polar Lipids, Alabaster, Ala.).

Optionally, dehydrated alcohol and propylene glycol can be used as co-solvents of the lipid phase, and vitamin E acetate can be included as an anti-oxidant. In various embodiments, other lipids or lipid-like substances are used in the invention, such as ceramides, lecithins, phosphatidyl ethanolamines, phosphatidyl serines, cardiolipins, trilinoleins and like compounds. Nonphospholipids may also be used in the present invention. For example, nonphospholipid materials that may be useful include lipid vesicle forming polyoxyethylene fatty esters, polyoxyethylene fatty acid ethers, diethanolamines, long-chain acyl amides, long-chain acyl amino acid amides, long-chain acyl amides, polyoxyethylene sorbitan oleates, polyoxyethylene glycerol monostearates, glycerol monostearates, and mixtures, analogs, and derivatives thereof. The vesicles may also include a steroid, and a charge producing agent. Preferred steroids include cholesterol, hydrocortisone, and analogs, derivatives, and mixtures thereof. Preferred negative charge producing materials are oleic acid, dicetyl phosphate, palmitic acid, cetyl sulphate, retinoic acid, phosphatidic acid, phosphatidyl serine, and mixtures thereof. In order to provide a net positive charge to the vesicles when desired, long chain amines, e.g., stearyl amines or oleyl amines, long chain pyridinium compounds, e.g., cetyl pyridinium chloride, quaternary ammonium compounds, or mixtures of these can be used, so long as the lipid vesicle can carry sufficient quantities of the aqueous phase.

Other liposomal formulations, including non-phospholipid lipsomes, may be utilized in the invention. For general reference, the multiphase liposomal drug delivery system disclosed in U.S. Pat. No. 4,761,288, issued Aug. 2, 1988 to Mezei (the disclosure of which is incorporated herein for ease of reference), is an exemplary representative of liposome compositions that may be utilized in the invention. For use as a topical carrier, modification of the liposome (or other lipid vesicle utilized in the invention) to sterically stabilize the vesicle, or to provide for targeting, or to provide the vesicle (or other lipid-based carrier utilized) with slow release properties, may interfere with the topical activity of the composition, and is therefore not preferred.

There is no theoretical limit to the number of compounds that may be incorporated into a lipid-based carrier for use in the invention. However, as those of ordinary skill in the art are aware, encapsulation efficiency is generally greater in liposomal compositions having a relatively high lipid:water content and a lipid-soluble drug carried in a lipid phase may generally be provided in a higher concentration than a water-soluble drug carried in an aqueous phase.

For example, two or more ingredients can be encapsulated in the same vesicle, or if the active compounds are incompatible, the compounds can be encapsulated separately and the topical carrier compositions combined to provide a composition with two or more indications, or that treats a single indication with multiple active compounds.

It is also possible to contemporaneously treat the external auditory canal by administering a topical carrier composition including one or more active compounds for treatment of the outer ear canal encapsulated in a vesicle, and a second set of one or more active compounds for treating the auditory canal dispersed in unencapsulated form in a surrounding water phase. Or, alternatively, non-vesicular lipids may be present, and all actives not encapsulated.

Preferably, compositions of the invention are provided in a slow release form, such as in liposomes manufactured to resist degradation. Those of ordinary skill in the art will be familiar with methods of manufacture that will accomplish this goal including, without limitation, addition of cholesterol to the lipid phase (see, e.g., U.S. Pat. No. 6,352,716, incorporated herein by reference as an illustration of a method for incorporating cholesterol into liposomes to this end).

Such relatively insoluble lipid vesicles can be expected to remain where delivered, to slowly release one or more of the active agents. Such vesicles may also have disinfectant or other properties helpful in treating or controlling the rate of infection in the outer ear; e.g., if hexadecyl trimethylammonium bromide, a potent disinfectant, is utilized as a positive charge producing material within the vesicles provides a secondary advantage. In such embodiments, the vesicles act as a sustained release formulation as they each deteriorate.

C. Useful Active Agents for Treatment and Prophylaxis of Otitis Externa

By "active agent" is meant any biologically active compound useful in the treatment and/or prevention of otitis externa and its sequalae, as well as associated pain and inflammation. In this respect, therefore, particularly preferred medicaments are antibiotics useful in the treatment or prevention of otitis externa in mammals, especially humans. Depending on the severity of the condition and its cause, such antibiotics include, without limitation, amoxicillin (and other penicillins), ciprofloxacin (and other quinolone antibiotics, such as ofloxacin), clavulanate (and other beta-lactamase inhibitors), cefaclor (and other cephalosporins, such as cefixime), azithromycin (and other macrolide antibiotics, such as clarithromycin), and sulfisoxazole (as well as other sulfa drugs, such as sulfamethoxazole). Of the antibiotics useful in the invention, those that are highly lipid soluble, which may be water insoluble, are preferred, with thiamphenicol and its analogues (e.g., chloramphenicol) being especially preferred.

Preferably, compositions of the invention will contain multiple agents useful in treating otitis externa including, without limitation, anti-fungal and anti-inflammatory compounds. Useful anti-inflammatory compounds for co-administration or use independent of antibiotic therapy include those that are sometimes less effective or well-tolerated in oral administration; e.g., non-steroidal anti-inflammatory drugs (NSAIDs), such as diclofenac, naproxen, ketoprofen, celecoxib, indomethacin, and pharmaceutically acceptable derivatives thereof. Steroidal compounds may be administered as an alternative or additive to a NSAID when clinically indicated (e.g., in chronic cases of otitis externa with pruritis), but are not required for use in the invention. Where present, the steroid may be betamethasone, betamethasone dipropionate, fluocinonide, fluocinoline acetonide, hydrocortisone, methylprednisolone, clobetasol, beclomethasone, dexamethasone sodium phosphate, triamcinolone and pharmaceutically acceptable derivatives thereof.

In preferred embodiments, the pharmaceutically active agents provided will include an anti-fungal agent. Suitable anti-fungal agents primarily include those that act on the cell wall or membrane of the fungi, although others (e.g., intracellularly acting agents) may also be suitable when clinically indicated. In general, cell wall/membrane active anti-fungals include the allylamines, the azoles, the polyene antimicotics, and the echinocandins. Non-limiting specific examples include terbinafine, miconazole, ketoconazole, amphotericins, fluconazole, flucytosine, natamycin, amphotericin B, nystatin, cromolyn, lodoxamide, levocabastin, naphazolin, antazoline, pheniramimane and pharmaceutically acceptable derivatives thereof. Unless its use is contraindicated (e.g., for certain lupus patients), terbinafine is the presently preferred anti-fungal agent for use in the invention.

In some embodiments the pharmaceutically active agent may also include a local anesthetic or analgesic agent. Examples of suitable agents include benzocaine, benzyl benzoate, bupivacaine, calamine, chloroprocaine, chloroxylenol, cinchocaine, cocaine, dexivacaine, diamocaine, dibucaine, dyclonine, etidocaine, hexylcaine, ketamine, levobupivacaine, lidocaine, menthol, mepivacaine, oxethazaine, phenol, pramoxine, prilocalne, amethocaine, tetracaine, proparacaine, propoxycaine, pyrrocaine, resorcinol, risocaine, rodocaine, ropivacaine, tetracaine, and pharmaceutically acceptable derivatives thereof. Due to the rapid action of the compositions of the invention in resolving treated otitis externa, use of such anesthetic or analgesics may be unnecessary.

In animals especially, otitis externa is often linked to a parasitic infestation, most often an otocariosis, or *Otodectes cynotis* (ear mites) infestation. Topical treatment with ear mites has often been accomplished with relatively long courses of topical insecticidal therapy; e.g., with a pyrethrin-containing composition. However, shorter courses of therapy have been more recently obtained with mectin and mycin compounds; e.g., avermectins (such as ivermectin and selamectin) and milbemycin, administered otically, by injection, or on the skin. If clinically indicated, such anti-parasiticidal compounds may be co-administered within, or as a separate adjunct to, the compositions of the invention. Further, where clinically indicated, anti-viral compounds, such as acyclovir, may be administered in lieu of, or as an adjunct to, antibiotic compounds.

The following examples illustrate preparation and use of a preferred composition of the invention to treat otitis externa in dogs. As demonstrated, the condition was resolved in most animals with a single dose course of treatment. Animals who continued to show signs of the condition at day 14 following treatment were given another dose, and the condition resolved.

It will of course be appreciated that the invention may be utilized to treat otitis externa in any mammal, in whom the pharmaceutically acceptable, cellulose-free, non-gelled compositions of the invention will be applied topically to the outer ear canal in a dose sufficient to clinically ameliorate (significantly reduce symptoms to susceptibility to resolution with re-treatment, preferably a single dose re-treatment) or to resolve the treated condition. While physicians and veterinarians will of course be familiar with appropriate concentrations for dosing with individual active agents, the concentrations and dosing ranges expected to be efficacious in most clinical situations and species are 0.1 to 2.0% active w/w, delivered in unit dosages of up to about 1 mls., or 10-20 drops depending on the clinician's judgment of the appropriate course of treatment and the strength of the dosage delivered.

The invention having been fully described, the following examples are intended to illustrate, not to limit, the scope of the invention, which is defined by the appended claims.

EXAMPLE 1

Antibiotic, Anti-Fungal, NSAID-Containing Composition of the Invention

The lipid carrier was prepared with phospholipon 90H, and the active/inactive ingredients listed admixed therewith to a volume of 100 g as follows.

For preparation of the aqueous phase, water was added to a stainless steel jacketed vortex hydration chamber mixing vessel. The vessel's chamber was covered to prevent evaporation of water and equipped with a bottom port and valve to regulate flow of material out of the vessel. For Formulation 1B, the DOWCIL™ 200 was added and dissolved into the water. For both formulations, one-half of the thiamphenical was added and dissolved to the water, and heat applied to the mixture at 50° C.+−2° C. Mixing was performed at low speed to avoid formation of a foam. As the mixture was heating, the diclofenac was added and mixed until dissolved. Once the mixture reached a temperature of 50° C.+−2° C., the xanthan gum was slowly added to the vortex as mixing continued until all ingredients were dissolved or (as to the gum) fully hydrated. The temperature was raised and mixing completed when the mixture reached a temperature between 55° C. and 60° C.

For preparation of the lipid phase, a second stainless steel jacketed mixing vessel was utilized in close proximity to the first. In this second vessel, mixing of the propylene glycol, alcohol, cholesterol, vitamin E acetate, terbinafine and the remaining half of the thiamphenicol with the phospholipon 90H was initially performed slowly to avoid formation of foam or surface bubbles. An overhead mixer was started and heat applied to raise the temperature of the mixture to between 55° C. and 60° C. until all were dissolved. A cover was used on the chamber to prevent evaporation of alcohol throughout the procedure.

The lipid phase was quickly added to the aqueous phase at medium mixing speed. In particular, valves were opened on the bottom ports of the chambers, and the flow was regulated from both vessels. The aqueous phase and oil phase flowed and met at an in-line regulating tee, and a dispersing pump pulled the two phases together. The mixture was circulated through a 60 mesh dispersing screen to optimize the hydration of the lipid phase. The mixture was then directed to the top of the chamber and the entire process was circulated through the pump, back into the chamber for 10 minutes.

After circulation, the chamber jacket was allowed to cool with continued slow mixing until the temperature of the product was 40° C., completing the process. The combination of materials is preferably fast enough to mix thoroughly without causing formation of surface foam or bubbling. The cooling process is preferably slow, with cooling of about 6° C. per hour most preferable, by pouring or quickly pumping the former into the latter to mix them using bottom ports and tees. No heat was applied to the mixture. The formulations prepared were as follows.

| FORMULATION 1A | | |
|---|---|---|
| Ingredient | Volume w/w % | Comments |
| Terbinafine HCL | 1.5 | |
| Thiamphenicol | 1.0 | ½ dissolved in oil, ½ in water prior to admixture |
| Diclofenac Sodium | 0.5 | |
| Phospholipon 90H | 4.5 | |
| Cholesterol | 0.2 | |
| Vitamin E Acetate | 1.0 | |
| Propylene Glycol | 5.0 | |
| Water | 80.18 | |
| Alcohol | 6.0 | |
| Xanthan Gum | 0.1 | |

The following composition, which included a preservative and a lower concentration of terbinafine, is slightly less efficacious, suggesting that lower concentrations of the anti-fungal agent may be utilized, still allowing for single dose resolution of treated ears.

| FORMULATION 1B | | |
|---|---|---|
| Ingredient | Volume w/w | Comments |
| Terbinafine HCL | 1.0 | Dissolved in oil |
| Thiamphenicol | 1.0 | ½ dissolved in oil, ½ in water prior to admixture |
| Diclofenac Sodium | 0.5 | Dissolved in water |
| Phospholipon 90H | 3.5 | |
| Cholesterol | 0.2 | |
| Vitamin E Acetate | 1.0 | |
| Propylene Glycol | 5.0 | |

-continued

FORMULATION 1B

| Ingredient | Volume w/w | Comments |
|---|---|---|
| Water | 81.58 | |
| Alcohol | 6.0 | |
| Xanthan Gum | 0.1 | |
| DOWCIL ™ 200 | 0.02 | |

EXAMPLE 2

Treatment of Otitis Externa in Canines

Twenty-six dogs of varying breeds with confirmed otitis externa, including bacterial infection, fungal infestation and inflammation, were treated with a single dose of the compositions of Example 1 by dropper-wise administration of 20 drops per ear. Dogs 1-16 were given Formulation 1B, while dogs 17-26 were given Formulation 1A. The treated ears were evaluated for signs of otitis externa at days 7 and 14 following dosing.

The endpoint for effectiveness was an clinical score improvement to 2 or less in both ears, with a presenting score of at least 6 per ear being a condition for admission of an animal into the study. The clinical scores were objectively assigned and evaluated by a clinician based on a standard scoring system for each of the following signs of otitis externa: pain, erythema, exudate, swelling, odor, and ulceration. The scores were assignable as follows: PAIN: 0=none, 1=mild/moderate—painful on palpitation, 2-severe—painful on raising of the pinna. ERYTHEMA: 0=none, 1=mild/moderate—barely noticeable to obvious redness on otoscopic evaluation, 2=severe—beet or bright red on examination and/or erythema extends into the pinna tissue. EXUDATE: 0=none, 1=mild/moderate—small amount visible in the ear canal, 2=severe—extends out of the ear canal and may be crusted. SWELLING: 0=none, 1=mild/moderate—some occlusion of the ear canal, 2—severe—ear canal completely occluded. ODOR: 0=none, 1=mild/moderate—malodor detectable when pinna is raised, 2=severe—malodor detectable without raising pinna. ULCERATION: 0=none, 1—mild/moderate—mild abrasions visible, 2=severe—abrasions extensive and/or may be bleeding.

One animal treated with Formulation 1B showed signs of particularly significant infection and was retreated at day 7. Yeast overgrowth was noted in two animals treated with Formulation 1B at day 14, so they were also retreated. No retreatment of animals who received Formulation 1A was required, although treatment was considered to fail (no significant amelioration or full recovery) in one such animal.

Overall, response to the treatment was not statistically significant in four animals by day 14. Possible reasons for treatment failure include presence of bacteria or fungus that wasn't susceptible to the active agents involved or other factors. In all four animals, the otitis externa presented as very severe, a 12 out of a scale of 12.

In nineteen of the animals, however, the otitis externa was completely resolved by day 14 following the single dose administered. All of those animals showed significant signs of improvement in the treated condition by day 7, including animals in whom the presenting condition was rated 12 on the 12 point scale.

| | | Ratings at Approximately 0, 7, & 14 Days (Formulation 1A) | | | | | |
|---|---|---|---|---|---|---|---|
| | | Visit 1 (Day 0) | | Visit 2 (Day 7) | | Visit 3 (Day 14) | |
| No. | Dog Name | Date | Rating | Date | Rating | Date | Rating |
| 1 | Puggles | 3/30 | 8 | 4/8 | 2 | 4/20 | 2 |
| 2 | Sadie | 3/31 | 12 | 4/8 | 3 | 4/30 | 11 * |
| 3 | Marley | 4/13 | 10 | 4/21 | 1 | 4/27 | 0 |
| 4 | Lilly | 4/15 | 10 | 4/23 | 2 | 4/30 | 1 |
| 5 | Cinder | 4/15 | 12 | 4/22 | 3 | 4/29 | 2 |
| 6 | Talbert | 4/28 | 12 | 5/5 | 4 | 5/12 | 7 * |
| 7 | Callie | 4/30 | 11 | 5/7 | 2 | 5/14 | 2 |
| 8 | Sandy | 5/5 | 12 | 5/14 | 6 R | 5/21 | 6 R(y)* |
| 9 | Sasha | 5/5 | 11 | 5/12 | 3 | 5/19 | 1 R(y) |
| 10 | Cinnamon | 5/12 | 9 | 5/19 | 1 | 5/26 | 1 |
| 11 | Chuck | 5/12 | 11 | 5/18 | 1 | 5/26 | 0 |
| 12 | Patches | 5/14 | 12 | 5/20 | 2 | 5/28 | 0 |
| 13 | Brigley | 5/18 | 9 | 5/28 | 1 | 6/3 | 0 |
| 14 | Blanca | 5/21 | 9 | 5/29 | 2 | 6/15 | 2 |
| 15 | Angel | 5/21 | 11 | 5/27 | 1 | 6/3 | 0 |
| 16 | Wiggles | 5/26 | 12 | 6/2 | 3 | 6/9 | 6 * |
| 17 | Sophia | 6/9 | 9 | 6/16 | 2 | 6/23 | 0 |
| 18 | Nokie | 6/10 | 8 | 6/15 | 2 | 6/22 | 0 |
| 19 | Sasha | 6/15 | 9 | 6/23 | 0 | 7/1 | 0 |
| 20 | Tank | 6/17 | 12 | 6/24 | 2 | 7/1 | 2 |
| 21 | Pearl | 6/17 | 10 | 6/24 | 2 | 7/6 | 2 |
| 22 | Bosco | 6/18 | 12 | 6/22 | 3 | 7/6 | 0 |
| 23 | Jasmine | 6/22 | 12 | 6/29 | 0 | 7/8 | 0 |
| 24 | Lucky | 6/24 | 11 | 7/1 | 2 | 7/8 | 4 |
| 25 | Kittie | 6/29 | 11 | 7/6 | 2 | 7/13 | 0 |
| 26 | Marley | 6/29 | 12 | 7/7 | 5 | 7/14 | 8 * |

R = retreat
R(Y) = yeast, retreated
* = failed

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are set forth within the following claims.

In addition, where features or aspects of the invention are described in terms of Markush groups, those skilled in the art will recognize that the invention is also thereby described in terms of any individual member or subgroup of members of the Markush group.

The scope of our invention is defined by the following claims.

What is claimed is:

1. A method for treating an existing otitis externa infection and sequelae thereof in a mammal, comprising topically applying a single dose of a pharmaceutically acceptable composition to the outer ear canal of the mammal to resolve the infection within 14 days of dosing, wherein the composition:
   (i) does not include viscosity-enhancing celluloses or adhesive components,
   (ii) is not in the form of a gel; and
   (iii) comprises a lipid carrier and at least two active agents selected from the group consisting of antibiotics, anti-fungals, anti-parasitics, anti-virals, non-steroidal anti-inflammatories, analgesics, anesthetics and steroids.

2. The method according to claim 1, wherein the lipid carrier is a lipid vesicle.

3. The method according to claim 1, wherein one active agent in said composition is an antibiotic.

4. The method according to claim 1, wherein one active agent in said composition is an anti-fungal.

5. The method according to claim 1, wherein one active agent in said composition is a non-steroidal anti-inflammatory drug (NSAID).

6. The method according to claim 3, wherein the antibiotic is selected from the group consisting of quinolone antibiotics, penicillin antibiotics, macrolide antibiotics, cephalosporin antibiotics, sulfa antibiotics, and beta-lactamase inhibitors.

7. The method according to claim 6, wherein said antibiotic comprises thiamphenicol.

8. The method according to claim 4, wherein said anti-fungal is an allylamine anti-fungal agent.

9. The method according to claim 8, wherein the allylamine is terbinafine.

10. The method according to claim 5, wherein the NSAID is diclofenac.

11. The method according to claim 1, wherein the active agents are an antibiotic, an anti-fungal and a NSAID.

12. The method according to claim 1, wherein the antibiotic is thiamphenicol, the anti-fungal is terbinafine and the NSAID is diclofenac.

13. The method according to claim 12, wherein the terbinafine is provided in a concentration of 1 to 1.5% w/w of the composition.

14. The method according to claim 12, wherein the diclofenac is provided in a concentration of 0.5% w/w of the composition.

15. The method according to claim 12, wherein the composition further includes an oil-insoluble preservative.

16. The method of claim 1, wherein the infection and sequelae thereof are clinically resolved within 14 days of administration.

* * * * *